(12) United States Patent
Niu et al.

(10) Patent No.: US 10,106,794 B2
(45) Date of Patent: Oct. 23, 2018

(54) RNA HYDROGEL

(71) Applicant: The Research Foundation for the State University of New York, Albany, NY (US)

(72) Inventors: Li Niu, Loudonville, NY (US); Zhen Huang, Latham, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 15/477,498

(22) Filed: Apr. 3, 2017

(65) Prior Publication Data
US 2017/0335319 A1  Nov. 23, 2017

Related U.S. Application Data

(63) Continuation-in-part of application No. PCT/US2015/054942, filed on Oct. 9, 2015.

(60) Provisional application No. 62/061,757, filed on Oct. 9, 2014.

(51) Int. Cl.
*C12N 15/11* (2006.01)
*C12N 15/113* (2010.01)
*G01N 33/545* (2006.01)
*C12Q 1/68* (2018.01)
*A61K 38/00* (2006.01)

(52) U.S. Cl.
CPC .............. *C12N 15/113* (2013.01); *C12Q 1/68* (2013.01); *G01N 33/545* (2013.01); *A61K 38/00* (2013.01); *C08G 2210/00* (2013.01)

(58) Field of Classification Search
None
See application file for complete search history.

(56) References Cited

U.S. PATENT DOCUMENTS

2008/0138408 A1* 6/2008 Venkatesh .............. A61K 31/70
424/464

* cited by examiner

*Primary Examiner* — Ekaterina Poliakova-Georgantas
(74) *Attorney, Agent, or Firm* — Heslin Rothenberg Farley & Mesiti P.C.; Kathy Smith Dias, Esq.

(57) ABSTRACT

The disclosure relates to synthetic oligonucleotides that are unique in that they are RNA molecules that have the capacity to form a hydrogel. Also disclosed are DNA oligonucleotides that encode the RNA oligos so that the oligos can be prepared using in vitro transcription. The disclosure further pertains to pharmaceutical compositions comprising these hydrogels.

12 Claims, 13 Drawing Sheets
Specification includes a Sequence Listing.

CZ (99 nt, MW 32415.5)
5'-GGGAGAAUUCAACUGCCAUCUAGGCGGCGCAAAAAACGUAA
AAUGGGUCAUGGGAAAGGGCAGGUGAGAGGACUAGUACUACA
AGCUUCUGGACUCGGU-3' (SEQ ID NO:1)

2CZ (237 nt, MW 73097.5)
5'- GGGAGGCGGAUUCGAGAAUUCAACUGCCAUCUAGGCGGCG
CAAAAAACGUAAAAUGGGUCAUGGGAAAGGGCAGGUGAGAGG
ACUAGUACUACAAGCUUCUGGACUCGGAUCCGUGACCCAAAGG
UCAUACUCCCGGAGAAUUCAACUGCCAUCUAGGCGGCGCAAAA
AACGUAAAAUGGGUCAUGGGAAAGGGCAGGUGAGAGGACUAG
UACUACAAGCUUCUGGACUCCAAUAUU-3' (SEQ ID NO:2)

FIGURE 1A

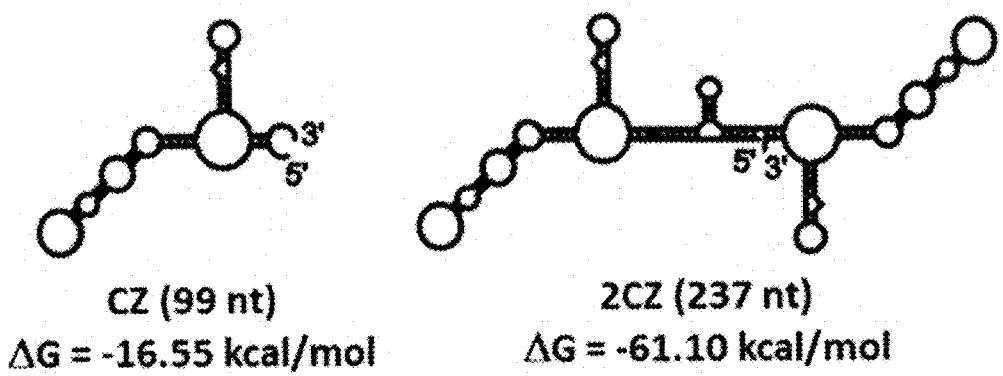

CZ (99 nt)
ΔG = -16.55 kcal/mol

2CZ (237 nt)
ΔG = -61.10 kcal/mol

FIGURE 1B

SEQUENCE LISTING

```
<160> NUMBER OF SEQ ID NOS: 18

<210> SEQ ID NO 1
<211> LENGTH: 99
<212> TYPE: RNA
<213> ORGANISM: Artificial Sequence
<220> FEATURE:
<223> OTHER INFORMATION: synthetic oligonucleotide

<400> SEQUENCE: 1
gggagaauuc aacugccauc uaggcggcgc aaaaaacgua aaaugggauca ugggaaaggg      60 caggugagag gacuaguacu acaagcuucu ggacucggu                             99

<210> SEQ ID NO 2
<211> LENGTH: 237
<212> TYPE: RNA
<213> ORGANISM: Artificial Sequence
<220> FEATURE:
<223> OTHER INFORMATION: synthetic oligonucleotide

<400> SEQUENCE: 2
gggaggcgga uucgagaauu caacugccau cuaggcggcg caaaaaacgu aaaaugggauc      60 augggaaagg gcaggugaga ggacuaguac uacaagcuuc uggacucgga uccgugaccc     120
aaaggucaua cucccggaga auucaacugc caucuaggcg gcgcaaaaaa cguaaaaugg     180
gucaugggaa agggcaggug agaggacuag uacuacaagc uucuggacuc caauauu        237

<210> SEQ ID NO 3
<211> LENGTH: 116
<212> TYPE: DNA
<213> ORGANISM: Artificial Sequence
<220> FEATURE:
<223> OTHER INFORMATION: synthetic oligonucleotide

<400> SEQUENCE: 3
taatacgact cactataggg agaattcaac tgccatctag gcggcgcaaa aaacgtaaaa       60
tgggtcatgg gaaagggcag gtgagaggac tagtactaca agcttctgga ctcggt         116

<210> SEQ ID NO 4
<211> LENGTH: 249
<212> TYPE: DNA
<213> ORGANISM: Artificial Sequence
<220> FEATURE:
<223> OTHER INFORMATION: synthetic oligonucleotide

<400> SEQUENCE: 4
taatacgact cactataggg aggcggattc gagaattcaa ctgccatcta ggcggcgcaa       60 aaacgtaaa atgggtcatg ggaaagggca ggtgagagga ctagtactac aagcttctgg      120
actcggatcc gtgacccaaa ggtcatactc ccggagaatt caactgccat ctaggcggcg     180
caaaaaacgt aaaatgggtc atgggaaagg gcaggtgaga ggactagtac tacaagcttc     240
``` tggactcca                                                              249

<210> SEQ ID NO 5
<211> LENGTH: 86
<212> TYPE: RNA
<213> ORGANISM: Artificial Sequence
<220> FEATURE:
<223> OTHER INFORMATION: synthethic oligonucleotide

<400> SEQUENCE: 5
ggagaauuca acugccaucu aggcggccga aaggucaugg gaaagggcag gugagaggac       60
uaguacuaca agcuucugga cucggu                                           86

<210> SEQ ID NO 6
<211> LENGTH: 93
<212> TYPE: RNA
<213> ORGANISM: Artificial Sequence
<220> FEATURE:
<223> OTHER INFORMATION: synthetic oligonucleotide

<400> SEQUENCE: 6
gggagaauuc aacugccauc uaggcggcgc aaaaaacgua aaaugggguca ugggaaaggg      60 caggugagag gacugaaaag cuucuggacu ccc                                   93

<210> SEQ ID NO 7
<211> LENGTH: 74
<212> TYPE: RNA
<213> ORGANISM: Artificial Sequence
<220> FEATURE:
<223> OTHER INFORMATION: synthetic oligonucleotide

<400> SEQUENCE: 7
gggagaauuc aacugccauc uaggcggcgc aaaaaacgua aaaugggguca ugggaaaggg      60 caggugggac uccc                                                        74

<210> SEQ ID NO 8
<211> LENGTH: 74
<212> TYPE: RNA
<213> ORGANISM: Artificial Sequence
<220> FEATURE:
<223> OTHER INFORMATION: synthetic oligonucleotide

<400> SEQUENCE: 8
gggagaauuc aacugccauc uaggcggcgc aaaaaacuua aaaugggguca ugggaaaggg      60 caggugggac uccc                                                        74

<210> SEQ ID NO 9
<211> LENGTH: 74
<212> TYPE: RNA
<213> ORGANISM: Artificial Sequence
<220> FEATURE:
<223> OTHER INFORMATION: synthetic oligonucleotide

<400> SEQUENCE: 9
gggagaauuc aacugccauc uaggcggcgc aaaaaaccua aaaugggguca ugggaaaggg      60 caggugggac uccc                                                        74

<210> SEQ ID NO 10
<211> LENGTH: 93
<212> TYPE: RNA
<213> ORGANISM: Artificial Sequence
<220> FEATURE:
<223> OTHER INFORMATION: synthetic oligonucleotide

```
<400> SEQUENCE: 10
gggagaauuc aacugccauc uaggcggcgc aaaaaacuua aaaugggucu ugggaaaggg    60
caggugagag gacugaaaag cuucuggacu ccc                                 93

<210> SEQ ID NO 11
<211> LENGTH: 93
<212> TYPE: RNA
<213> ORGANISM: Artificial Sequence
<220> FEATURE:
<223> OTHER INFORMATION: syntetic oligonucleotide

<400> SEQUENCE: 11
gggagaauuc aacugccauc uaggcggcgc aaaaaaccua aaaugggucu ugggaaaggg    60
caggugagag gacugaaaag cuucuggacu ccc                                 93

<210> SEQ ID NO 12
<211> LENGTH: 98
<212> TYPE: RNA
<213> ORGANISM: Artificial Sequence
<220> FEATURE:
<223> OTHER INFORMATION: synthetid oligonucleotide

<400> SEQUENCE: 12
gggagaauuc aacugccauc uaggcggcgc aaaaaacuua aaaugggucu ugggaaaggg    60
caggugagag gacuaguacu acaagcuucu ggacuccc                            98

<210> SEQ ID NO 13
<211> LENGTH: 98
<212> TYPE: RNA
<213> ORGANISM: Artificial Sequence
<220> FEATURE:
<223> OTHER INFORMATION: synthetic oligonucleotide

<400> SEQUENCE: 13
gggagaauuc aacugccauc uaggcggcgc aaaaaaccua aaaugggucu ugggaaaggg    60
caggugagag gacuaguacu acaagcuucu ggacuccc                            98

<210> SEQ ID NO 14
<211> LENGTH: 97
<212> TYPE: RNA
<213> ORGANISM: Artificial Sequence
<220> FEATURE:
<223> OTHER INFORMATION: synthetic oligonucleotide

<400> SEQUENCE: 14
gggagaauuc aacugccauc uaggcggcgc aaaaaacgua aaaugggucu ugggaaaggg    60
cagacggcgc aaaaaacgua aaaugggucu ugcuccc                             97

<210> SEQ ID NO 15
<211> LENGTH: 99
<212> TYPE: RNA
<213> ORGANISM: Artificial Sequence
<220> FEATURE:
<223> OTHER INFORMATION: synthetic oligonucleotide

<400> SEQUENCE: 15
gggagaauuc aacugccauc uaggcggcgc aaaaaaaaaa aaaugggucu ugggaaaggg    60
caggugagag gacuaguacu acaagcuucu ggacucggu                           99

<210> SEQ ID NO 16
```

```
<211> LENGTH: 97
<212> TYPE: RNA
<213> ORGANISM: Artificial Sequence
<220> FEATURE:
<223> OTHER INFORMATION: synthetic oligonucleotide

<400> SEQUENCE: 16
gggagaauuc aacugccauc uaggcggcgc aaaaaaaaaa aaauggguca ugggaaaggg      60
cagacggcgc aaaaaaaaaa aaauggguca ugcuccc                              97

<210> SEQ ID NO 17
<211> LENGTH: 245
<212> TYPE: DNA
<213> ORGANISM: Artificial Sequence
<220> FEATURE:
<223> OTHER INFORMATION: synthetic oligonucleotide

<400> SEQUENCE: 17
gcatgctaat acgactcact atagggaggc ggattcgaga attcaactgc catctaggcg      60
gcgcaaaaaa cgtaaaatgg gtcatgggaa agggcaggtg agaggactag tactacaagc     120
ttctggactc ggatccgcct cccggagaat tcaactgcca tctaggcggc gcaaaaaacg     180
taaaatgggt catgggaaag ggcaggtgag aggactagta ctacaagctt ctggactcca     240
atatt                                                                245

<210> SEQ ID NO 18
<211> LENGTH: 249
<212> TYPE: DNA
<213> ORGANISM: Artificial Sequence
<220> FEATURE:
<223> OTHER INFORMATION: synthetic oligonucleotide

<400> SEQUENCE: 18
taatacgact cactataggg aggcggattc gagaattcaa ctgccatcta ggcggcgcaa      60 aaacgtaaa atgggtcatg ggaaagggca ggtgagagga ctagtactac aagcttctgg     120
actcggatcc gtgacccaaa ggtcatactc ccggagaatt caactgccat ctaggcggcg     180
caaaaaacgt aaaatgggtc atgggaaagg gcaggtgaga ggactagtac tacaagcttc     240
tggactcca                                                            249
```

RNA HYDROGEL

CROSS REFERENCE TO RELATED APPLICATIONS

This application is a continuation of PCT/US2015/054942 filed Oct. 9, 2015 and published on Apr. 14, 2016 as WO 2016/05792, which claims the priority of U.S. provisional application No. 62/061,757 filed Oct. 9, 2014; the contents of each are hereby incorporated by reference in their entirety into the present disclosure.

STATEMENT OF RIGHTS UNDER FEDERALLY-SPONSORED RESEARCH

This invention was made with government support under grant number W81XWH-09-1-0568 awarded by the U.S. Army Medical Research Materiel Command. The government has certain rights in the invention.

SEQUENCE LISTING

This application contains a Sequence Listing, created on Oct. 7, 2015 and modified on Apr. 23, 2018; the file, in ASCII format, is designated 0794151A_Sequence Listing_ST25.txt and is 6.47 KB in size. The file is hereby incorporated by reference in its entirety into the application.

TECHNICAL FIELD

The disclosure relates to hydrogels and in particular, RNA hydrogels.

BACKGROUND OF THE INVENTION

Hydrogels are water-saturated turgid materials and can be used for a wide range of applications such as tissue engineering scaffolds and drug delivery vehicles. Biomolecules, such as lipids, peptides, proteins, polysaccharides, and deoxyribonucleic acid (DNA), but not ribonucleic acid (RNA), have been found to form hydrogels.

SUMMARY OF THE INVENTION

In one aspect, the disclosure relates to a synthetic RNA oligonucleotide comprising the secondary structure of:

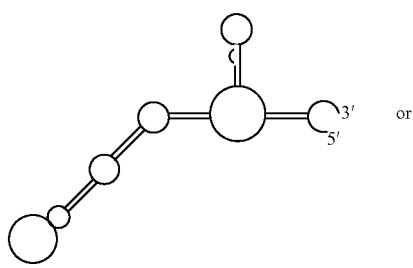

A or

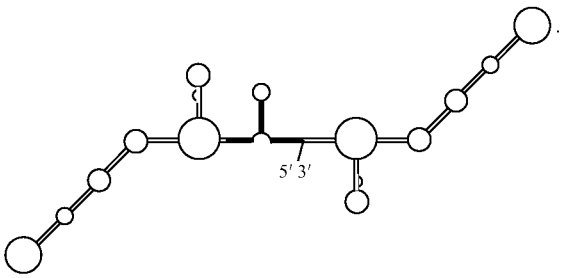

B

In one embodiment, the synthetic oligonucleotide consists of the nucleotide sequence of SEQ ID NO: 1 or SEQ ID NO: 2. These oligonucleotides form hydrogels.

In a related aspect, the disclosure relates to a synthetic oligonucleotide that encodes an RNA with the nucleotide sequence of SEQ ID NO: 1.

In yet another aspect, the disclosure relates to a synthetic oligonucleotide that encodes an RNA with the nucleotide sequence of SEQ ID NO: 2.

In yet another related aspect, the disclosure relates to a pharmaceutical composition comprising a synthetic oligonucleotide consisting of the nucleotide sequence of SEQ ID NO: 1 or SEQ ID NO: 2.

BRIEF DESCRIPTION OF THE DRAWINGS

FIGS. 1A-1D show characteristics of the RNA hydrogel of the disclosure including (A) nucleotide sequences of the CZ and 2CZ aptamers; (B) Mfold models for CZ and 2CZ aptamers; (C) in vitro transcription RNA samples of CZ and 2CZ (left) and the before (lane B) and after (lane A) PAGE purification sample of 2CZ (right). A 100-nt RNA marker was loaded on the side (lane M). (D) A pair of current traces from the GluA2 channel invoked by 0.1 mM of glutamate with/without the existence of 2 μM 2CZ. The potentiation ratio (A'/A) was ~2.

DETAILED DESCRIPTION OF THE INVENTION

Figure 1C:
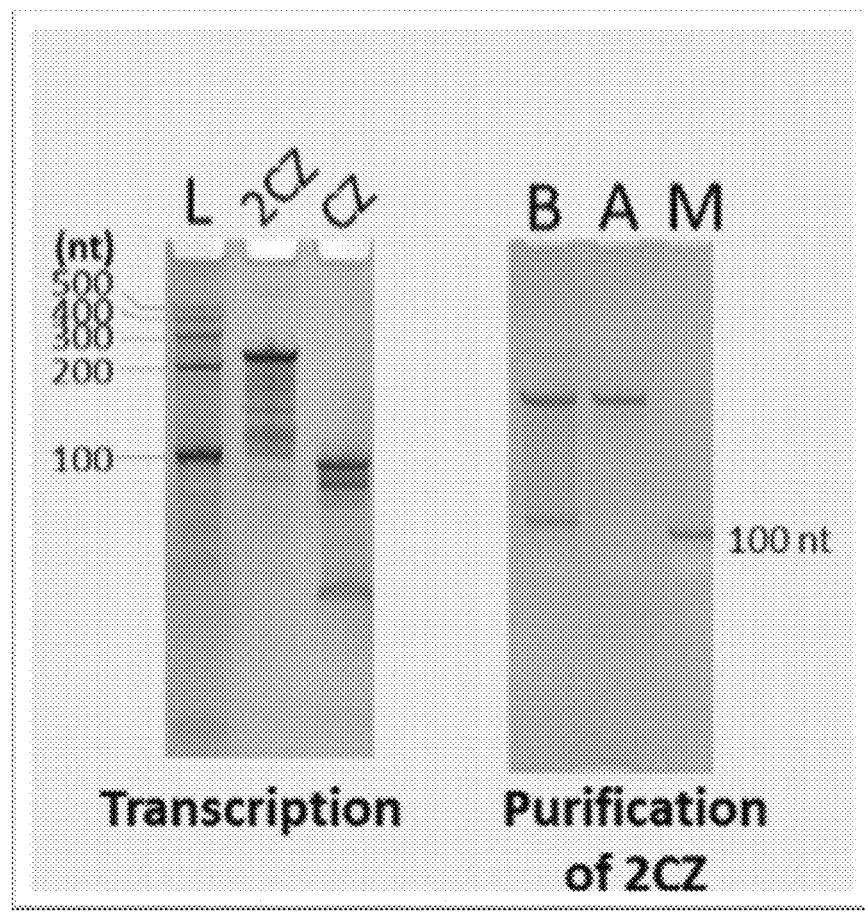

All patents, publications, applications and other references cited herein are hereby incorporated by reference into the present application. Methodology used in developing the present invention are well known to those of skill in the art and are described, for example, in Sambrook et al., 2001, Molecular Cloning: A Laboratory Manual, Third Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.), the contents of which are hereby incorporated by reference. In the description that follows, certain conventions will be followed as regards the usage of terminology.

Hydrogels are supramolecular assemblies hosting aqueous media with nearly identical solute transport properties of liquid and also mechanical properties of solid[1,2]. These properties make hydrogels uniquely useful, especially for biomedical applications, such as drug delivery vehicles[3-7].

Hydrogels have attracted considerable attention as promising biomaterials for various biotechnological and biomedical applications because of their high water content, favorable structural features and biocompatibility.

With the establishment of the first synthetic hydrogels by Wichterle and Lim in 1954[31], hydrogel technologies have become applicable to hygienic products[32], agriculture[33], drug delivery systems[32, 34], sealing[32], coal dewatering[35], artificial snow[32], food additives[36], pharmaceuticals[37], biomedical applications[36, 39] tissue engineering and regenerative medicines[40,41], diagnostics[42], wound dressing[43], separation of biomolecules or cells[44] and barrier materials to regulate biological adhesions[45], and biosensor[46].

Applications of particular interest in the present disclosure are those that include tissue engineering, drug delivery platforms, and cell culture scaffolds. Biocompatible hydrogels establish and regulate the mechanical properties of cells and tissues and thus serve as lubricants in joints or on epithelial surfaces. These gels can also serve as selective filters or selective barriers for a broader range of permeability control. In addition, hydrogels loaded with drugs can be used for wound dressing.

RNA Hydrogels

To date, all naturally occurring biomolecules are known capable of forming hydrogels or biocompatible hydrogels[3-6,8], except RNA. As the other type of nucleic acids, DNA can readily form hydrogels since the double stranded nature of DNA chains allows relatively intuitive design of network structures by base pairing interactions[9-11]. Specifically, short linear double-stranded DNA with designed sticky ends are synthesized as monomeric building blocks for hydrogels. In addition, these stick ends can be covalently linked as catalyzed by DNA ligases to join multibranched DNA monomers[10,11].

In contrast, RNAs are generally single stranded; they can form intra-strand double helixes and adopt complex tertiary structures, based on Watson-Crick base paring (guanine-cytosine or G-C and adenine-uracil or A-U), noncanonical base pairing (e.g., G-U or A-A) and complex tertiary interactions, such as base stacking, kissing loops and pseudo-knots[12,13]. As a result, RNA exhibits complex biological functions such as catalysis (please see The RNA World, 3rd ed.; Gesteland R. F., Cech T. R., Atkins J. F., Eds.; Cold Spring Harbor Laboratory (CSHL) Press: Cold Spring Harbor, N.Y., 2013.), inhibition[14] and regulation of gene expression[15]. However, RNA has not been known previously to either possess functional parts, similar to "sticky ends" in DNA hydrogels, or modular sequence segments as designer elements for network assembly through intermolecular interactions to form hydrogels. Here we describe an RNA whose sequence contains two unique sequence segments or motifs. The RNA can form hydrogel because of these sequence motifs. We show that these motifs are responsible for RNA self-assemblies to form a hydrogel network structure.

In one embodiment, an RNA molecule that can form a hydrogel has the nucleotide sequence of SEQ ID NO: 1:

```
CZ RNA (99 nt)
                                        (SEQ ID NO: 1)
5'-GGGAGAAUUC AACUGCCAUC UAGGCGGCGC AAAAAACGUA
AAAUGGGUCA UGGGAAAGGG CAGGUGAGAG GACUAGUACU
ACAAGCUUCU GGACUCGGU-3'
```

Initially, an RNA aptamer was selected from a library of ~10[14] sequences using SELEX, an in vitro evolution experiment[16,17] We initially aimed to find an RNA aptamer capable of positively enhancing AMPA receptor response to glutamate, the endogenous neurotransmitter in the central nervous system, thereby increasing the amplitude and/or the duration of synaptic responses in vivo. Positive modulation of AMPA receptors has long been suggested to affect cognition[18,19]. For instance, depolarization at dendritic spines (i.e., small appendages of dendrites) via AMPA channels is linked to the induction of long-term potentiation (LTP), a presumed substrate of memory[20]. Studies of the interaction between glutamatergic and monoaminergic systems suggest the link of a reduced glutamatergic transmission to certain cognitive disorders, such as schizophrenia and Parkinson's disease[21]. Potentiators of AMPA receptors are drug candidates in a treatment of cognitive disorders[22]. In our experiment, the in vitro selection target was GluA2, a key AMPA receptor subunit[23]. The receptors were transiently expressed in human embryonic kidney (HEK-293) cells, and the lipid membrane fragments that contained GluA2 receptors were used as the selection target[24].

Figure 1D:
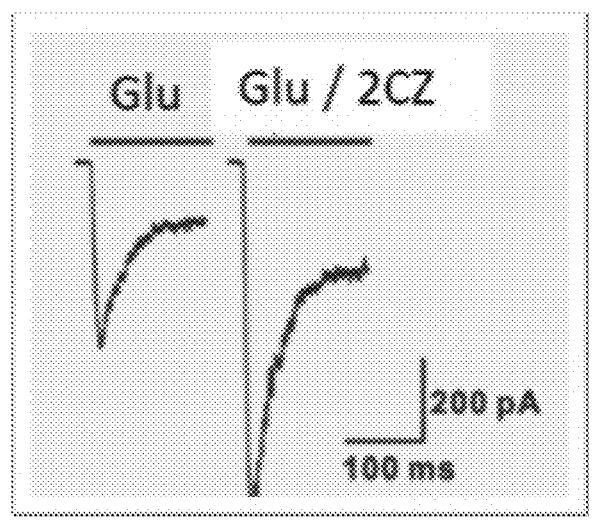

After a 12-round selection, an RNA, which we term "CZ aptamer" (the predicted secondary structure using MFold are shown in FIGS. 1A and 1B, respectively) was isolated. Using whole-cell current recording with the GluA2 expressed in HEK-293 cells, we found the purified RNA (FIG. 10) potentiated GluA2 response to glutamate (FIG. 1D, right panel) as compared with the control (FIG. 1D, left panel). Specifically, CZ aptamer potentiated the GluA2 channel by increasing current amplitude without slowing or blocking channel desensitization.

Surprisingly, CZ aptamer turned into an elastic solution state in a standard enzymatic transcription reaction mixture in just a few hours after transcription reaction was initiated. Motivated by this finding, a 237-nt 2CZ RNA whose sequence was essentially a double repeat of the CZ aptamer (see its predicted secondary structure in FIG. 1B) was prepared.

2CZ-RNA (237 nt)
(SEQ ID NO: 2)
5'-GGGAGGCGGA UUCGAGAAUU CAACUGCCAU CUAGGCGGCG

CAAAAAACGU AAAAUGGGUC AUGGGAAAGG GCAGGUGAGA

GGACUAGUAC UACAAGCUUC UGGACUCGGA UCCGUGACCC

AAAGGUCAUA CUCCCGGAGA AUUCAACUGC CAUCUAGGCG

GCGCAAAAAA CGUAAAAUGG GUCAUGGGAA AGGGCAGGUG

AGAGGACUAG UACUACAAGC UUCUGGACUC CAAUAUU-3'

Figure 2A:
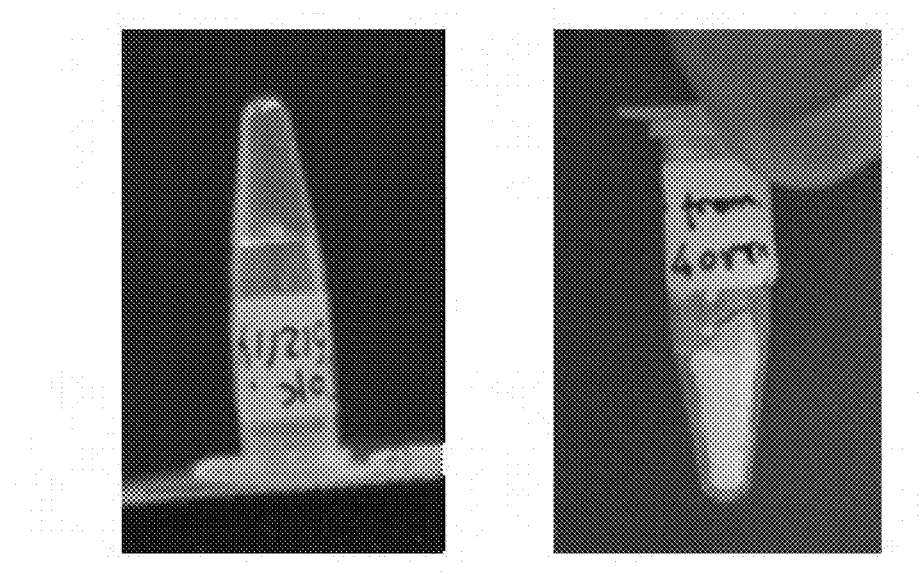
FIGS. 2A and 2B show photographs of the 2CZ hydrogel formed in a transcription mixture (A) Left photo: The hydrogel formed by 2.5% PAGE purified 2CZ with 2 mM MgCl$_2$ in an eppendorf tube. The TBE buffer after PAGE purification was replaced by 25 mM HEPES (pH 7.5) in a spin centrifuge tube filter. The MgCl$_2$ was added after the sample was transferred to the tubes. Right photo: The lyophilized CZ2 from an original 400 μl 2.5% hydrogel. (B) The thermocycle experiment on the 2CZ hydrogel formed in the transcription tube. The hydrogel in the tube melted when incubated under 65° C. and reformed when cooled down to room temperature.

Similarly to the CZ aptamer, 2CZ aptamer also formed an elastic solution state. To confirm that the RNA was responsible for the gel state, we purified the 2CZ RNA (lane 'A' of the right panel in FIG. 10). The purified 2CZ reconstituted in a buffer (i.e., 2.5±0.2%) in the presence of 2 mM $MgCl_2$ formed gel at room temperature (left panel in FIG. 2A and Table 1).

TABLE 1

Composition of 2CZ samples employed for material characterizations.

| Characterization Method | 2CZ RNA[a] (% w/v) | $MgCl_2$ in the Sample[b] (mM) |
| --- | --- | --- |
| Visual inspection[c] | 4% | 0 |
| | 2.5% | 2 |
| | 0.8% | 25 |
| Cryo-TEM[d] | 0.5% | 0, 2 |
| SAXS[e] | 1%, 2%, 4% | 0, 2, 5 |
| Rheology | 2.5% | 2 |

[a]2CZ RNA samples were purified from the in vitro transcription mixture, which contained 25 mM $MgCl_2$, by using a PAGE column electrophoretic elution method. The TBE buffer (Tris/borate/EDTA, pH 8.3) used in electrophoresis elution contained no $MgCl_2$. The TBE buffer was exchanged with 25 mM HEPES buffer (pH 7.5) in an Amicon centrifuge filter tube (50k Dalton cut off). The concentration of RNA was estimated based on the UV260 absorption value. A 2CZ RNA specimen of 1% concentration is 10 μg/μl or 137 μM.
[b]$MgCl2$ was added to the sample after RNA was purified and concentrated.
[c]visually identifiable hydrogel is judged by 1) the gel in the tube doesn't flow when tapping the bottom of the tube or inverting the tube 2) the gel doesn't flow when using a flat spatula to scoop it.
[d]0.5% 2CZ samples with/without 2 mM of $MgCl_2$ were tested separated.
[e]Each concentration of the 2CZ was prepared in 3 tubes with 0, 2, or 5 mM of $MgCl_2$, respectively.

Figure 2B:
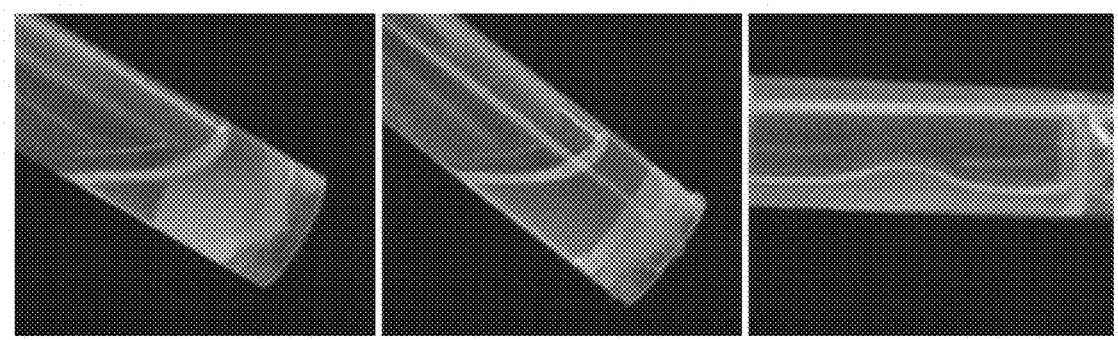

To further verify that 2CZ RNA could form hydrogel, we lyophilized the sample. Lyophilization of the RNA solution left sponge-like textured material in the tube with nearly similar volume before dehydration, indicating the RNA chains span all the solution volume (right panel, FIG. 2A). Heating this elastic solution to 65° C., for example, turned the gel into a clear viscous liquid and cooling to room temperature returned the solution to its initial state, indicating that sol-gel or gel-sol transitions are thermotropic (FIG. 2B). This was expected because the gelation of RNA was by self-assembly and no cross linker was involved. We found that the gelation depended on the concentration of both the RNA and salt. The critical concentration of gelation, identified by visual inspection of non-flowing behavior under gravity, for 2CZ aptamer was ~0.8% (weight) RNA/25 mM $MgCl_2$ or ~2.5% RNA/2 mM $MgCl_2$ or ~4% RNA without any $Mg^{2+}$ added to 25 mM HEPES buffer (pH 7.5 and 22° C.) (Table 1). Therefore, $Mg^{2+}$ was not critical in sol-gel transition (note that for transcription reaction to make 2CZ RNA, a minimal of 10 mM $Mg^{2+}+Cl_2$ was required). Furthermore, the gelation of a 2CZ sample was unaffected whether the sample was in a 50 mM Tris or HEPES buffer at pH 7.5 or 8.

Hydrogel Properties

Figure 3A:
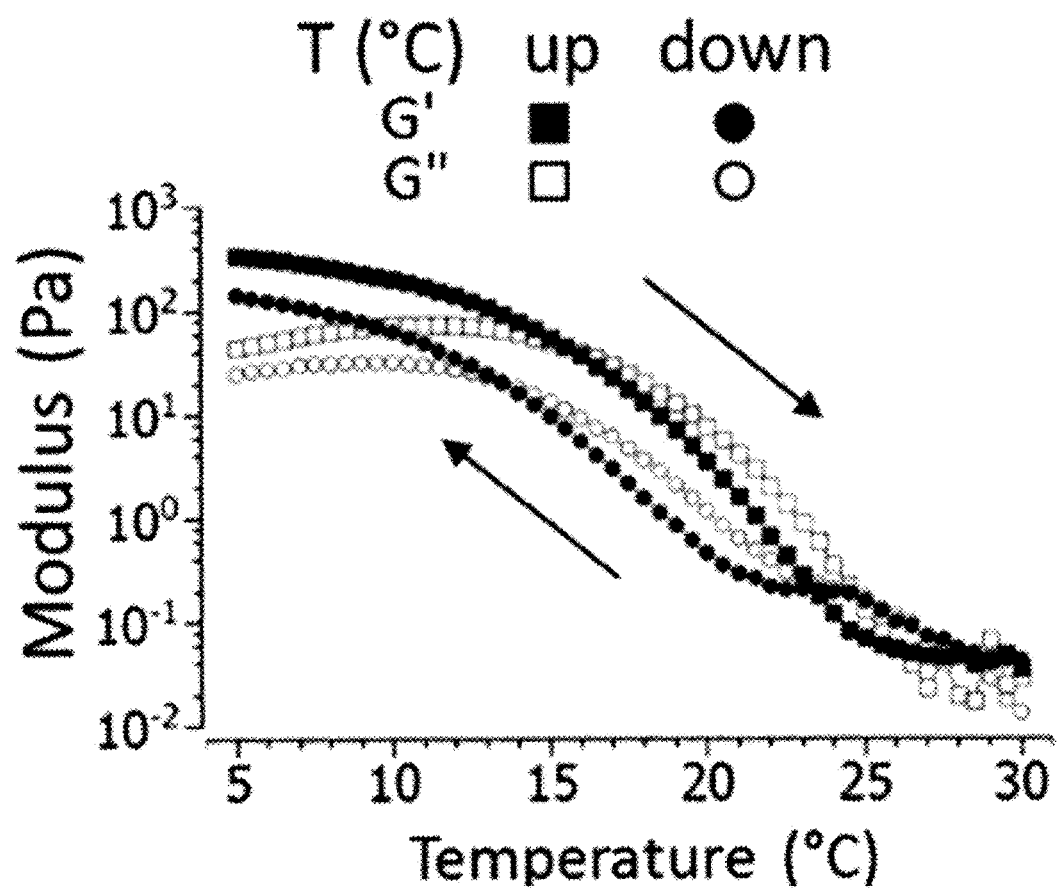
FIGS. 3A-3E (A) Temperature sweeping test on 2.5% 2CZ sample containing 2 mM MgCl$_2$. The experiment condition was maintained at a small amplitude oscillation of 1 rad/s, a strain of 1%, and a heating/cooling rate of 0.1° C./min. The G' and G" measured during temperature rose period were represented by solid and hollow rectangles, respectively. The G' and G" during the temperature dropping period were represented by solid and hollow circles, respectively. (B) The storage modules (G') collected from the frequency sweeping (0.1 to 100 rad/s at 1% strain) on the 2.5% 2CZ/2 mM MgCl2 sample under different temperatures (5-20° C.). (C) The loss modules (G") collected from the frequency sweeping (0.1 to 100 rad/s at 1% strain) on the 2.5% 2CZ/2 mM MgCl$_2$ sample under different temperatures (5-20° C.). (D) The Cryo-TEM images of 0.5% 2CZ in 25 mM HEPES (pH 7.5) with additional 2 mM $MgCl_2$. (E) The small angle X-ray scattering (SAXS) pattern collected from the 1%, 2%, and 4% 2CZ hydrogel containing 0, 2, or 5 mM $MgCl_2$.
Figure 3B:
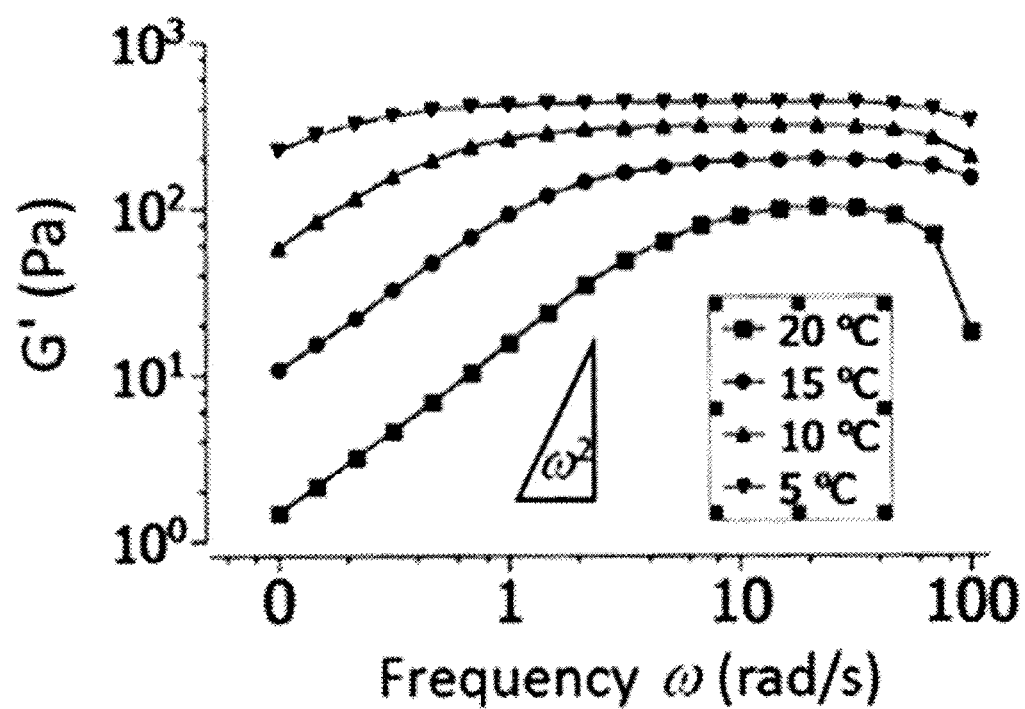
Figure 3C:
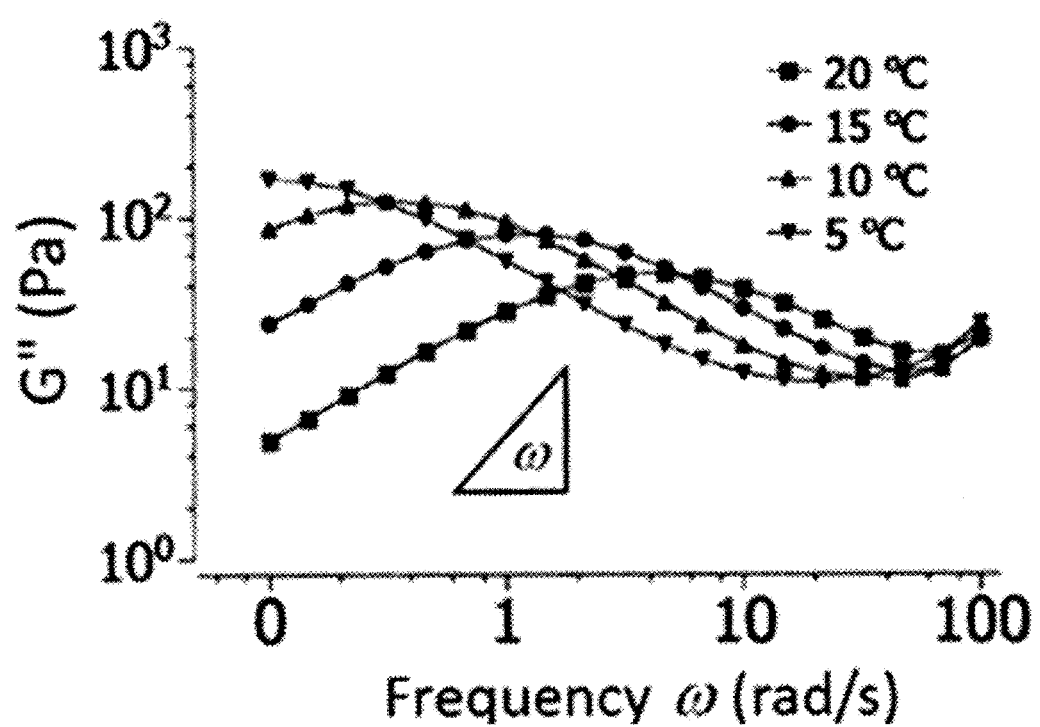

The viscoelastic properties of this hydrogel was investigated by employing a temperature sweep rheology test under the condition of small amplitude oscillation (1 rad/s) and strain (1%) at a heating/cooling rate of 0.1° C./min (FIG. 3A). The shear storage G' and loss G" moduli were relatively flat from 5° C. to ~15° C. and decayed as the sample was heated to 25° C. The G' and G" on cooling also appeared similar to the heating responses overall, but lower moduli indicated a moderate hysteresis existed. Dynamic sweeps from low to high frequency (ω) revealed more pronounced temperature-dependent viscoelastic properties. At 20° C., the G" increased steeply toward a brief plateau, and then a terminal regime appeared at low w region (FIG. 3B). As the temperature was lowered to 15, 10, and 5° C., the magnitude of G" plateau increased and the plateau became wider. In the terminal regime, however, the storage and loss moduli showed temperature independent scaling G'~$\omega^{1.0}$ and G"~$\omega^{0.78}$ in 5° C. to 20° C. (FIG. 3C). This terminal behavior suggests the existence of multiple relaxation modes on the time scale of a few seconds in the RNA hydrogel, similar to living worm-like micelles. The worm-like behavior is characteristic of self-assembling properties and dynamic growth of linear polymer chains or chain bundles in the viscoelastic regime. These results suggest that a mixture of populations of shorter "polymers" formed by 2CZ RNA prior to an extended hydrogel network, and the growth of these shorter "polymers" is dynamic.

Figure 3D:
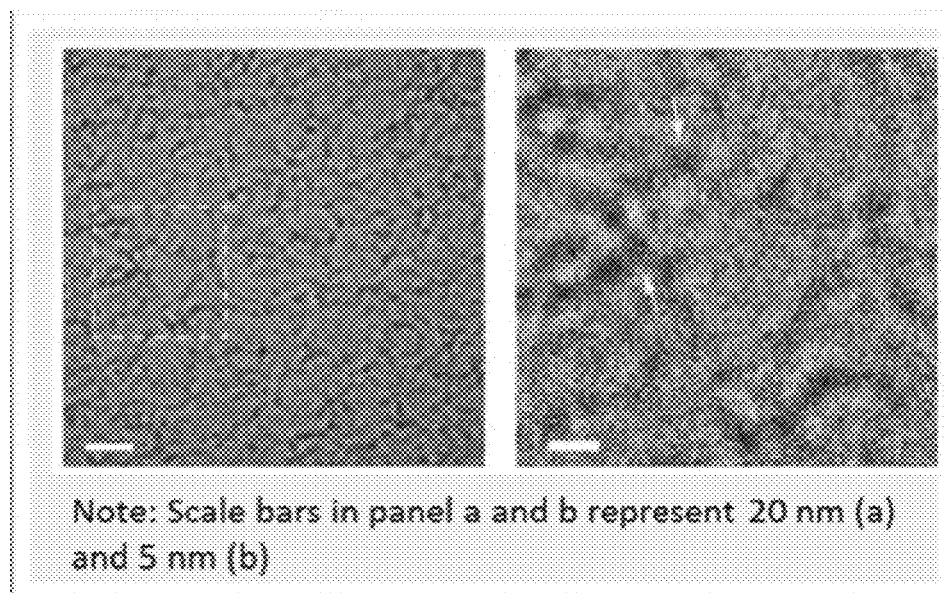
Figure 3E:
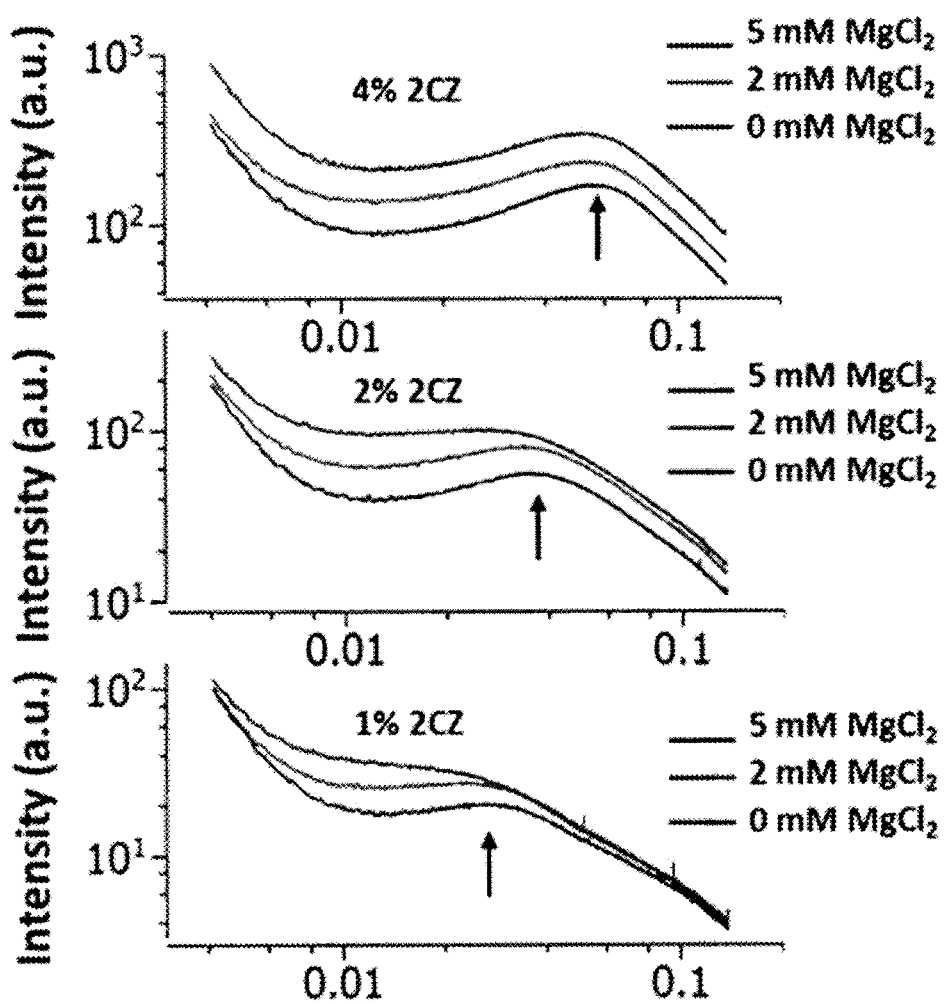

Next we carried out small angle X-ray scattering (SAXS) experiments to investigate spatial correlation of RNA hydrogel structures in solutions (FIG. 3E). Two dimensional X-ray scattering patterns of RNA hydrogel samples (1, 2, and 4% RNA in HEPES buffer with 0, 2, and 5 mM of $MgCl_2$) were collected at 25° C. These patterns were azimuthally integrated into one dimensional (1D) scattering intensity versus scattering vector q (where q=4π$\lambda^{-1}$ sin(θ), λ is the X-ray wavelength and θ is the scattering angle). All the 1D patterns showed a broad peak indicating concentration-dependent interdomain spacing of d≈23 nm at 1% (q*≈0.027 $Å^{-1}$), d≈17 nm at 2% (q*≈0.037 $A^{-1}$), and d≈11 nm at 3% (q*≈0.056 $Å^{-1}$) RNA samples (FIG. 3E). The peak positions varied by RNA concentration but the effect of $MgCl_2$ was more pronounced in the low RNA concentration as the intensities in the low q domains amplify. To identify the origin of domain-correlations in the SAXS patterns, we explored real space characterizations on a RNA solution of 0.5% in HEPES buffer with 2 mM $MgCl_2$ using cryogenic-transmission electron microscopy (FEI Tecnai G2 F30). High magnification micrograph revealed faint but unmistakable features of struts of undulating knot-like motifs (FIG. 3D). Although those knots are not visually distinct in every parts, distinctively recognizable domains showed spacing of approximately ~11 nm, which suggests the characteristic length scales identified by SAXS are the interdomain spacings of knot motifs along the axial directions of struts. In fact, this spacing does not perfectly match with the characteristic length scale for the RNA solution of low concentration (d≈23 nm at 1%) by SAXS. However, this discrepancy is likely caused by unequal visibility of motifs in struts on micrographs (alternatively a local concentration of RNA confined in TEM grids was different from the bulk concentration). In addition, any structural parts corresponding to the domain spacings identified by SAXS could not be identified on micrographs. Together our data show network structures by undulating struts connected with each other and more importantly, the imaged network structures confirm the origin of elastic properties of RNA solutions by selective associations of RNA chains.

Because the CZ RNA aptamer we discovered is uniquely capable of self-assembling to form hydrogel, a single RNA molecule must contain at least two unique sequence segments. These two sequence segments will enable a single RNA molecule as a "monomer" to bind non-covalently with the same sequence segments of at least two other RNA molecules so that RNA molecules could "grow" longer to form suprastructures, as the basis of hydrogel matrix. These unique sequence segments, possibly in motif forms, for inter-molecular interactions should be available after an RNA first folds intra-molecularly. To investigate the existence and the nature of these unique sequences, we first used MFold, an RNA secondary structure prediction program, to examine the CZ RNA "monomer" (we reasoned that a 2CZ RNA, as in FIGS. 1A and B, is a double repeat and it must certainly contain these sequence segments). By MFold, CZ aptamer folds into a structure with two apparent motifs: Motif 1 is a terminal loop and Motif 2 is the branched segment that contains a terminal loop, along with a bulge and a stem (see FIG. 4A, the colored regions as labeled). To characterize the role of these motifs and possibly identify single nucleic acid residues in gelation, we created a series of mutants and analyzed their gel-forming abilities. (a) Replacing either motif 1 or motif 2 (CZ.d2 in FIG. 4A) with a classic tetraloop[25] did not abolish the gel-forming ability of a corresponding mutant, although the mutant formed the gel much more slowly; (b) in fact, removing the entire motif 1 (CZ.d3 in FIG. 4A) was insufficient to abolish the gel-forming ability; and (c) eventually, a mutant with either a U or C that replaced G in motif 1 but without motif 2 (see the comparison between CZ.d3 and CZ.d5 or CZ.d6) was no longer capable of forming gel. These results suggest that both motifs are required in gelation but motif 1 is more important than motif 2.

Figure 4A:
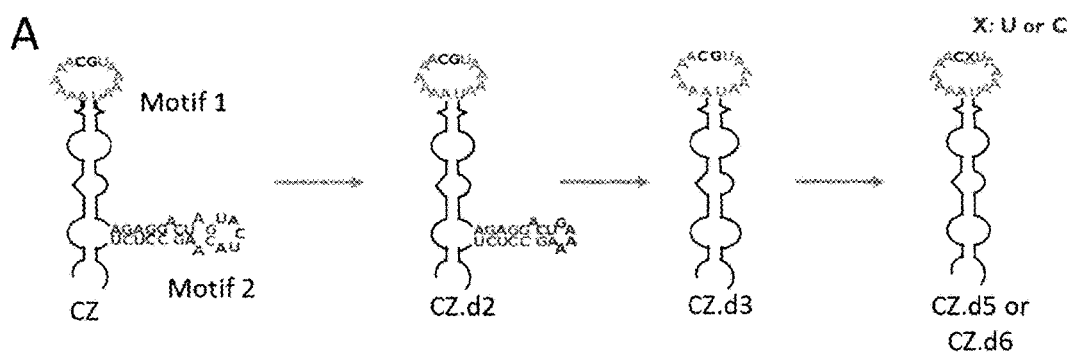
FIGS. 4A and 4B are schematics of oligonucleotide motifs 1 (SEQ ID NO: 19) and 2 (SEQ ID NO: 20) associated with aptamers of the disclosure.
Figure 4B:
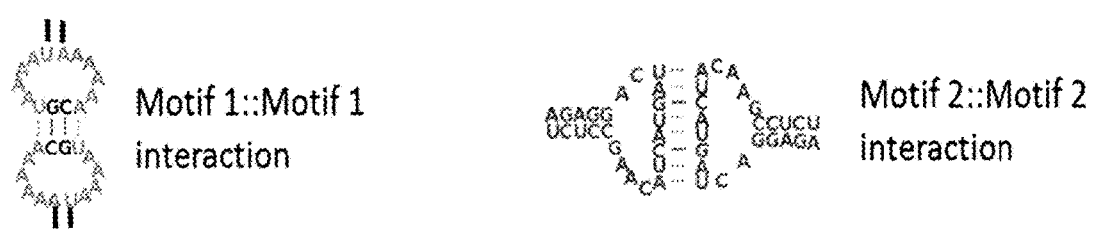
Figure 5:
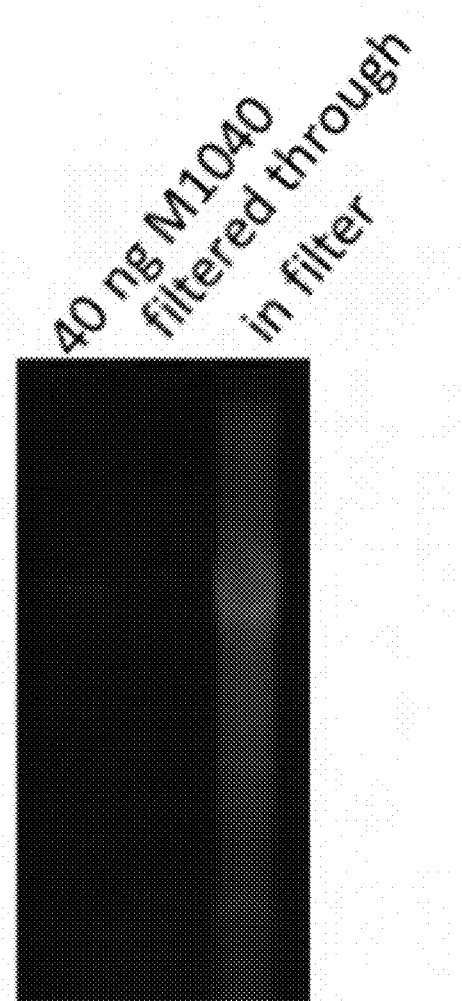
FIG. 5 An Amicon centrifuge filter tube with 50 k Dalton molecular weight cut off was used to concentrate the CZ RNA sample. The buffer flow through the filter contained no CZ RNA. Obviously the CZ RNA, the MW of which is 32.4 k Dalton, was all retained in the filter tube.
Figure 6A:
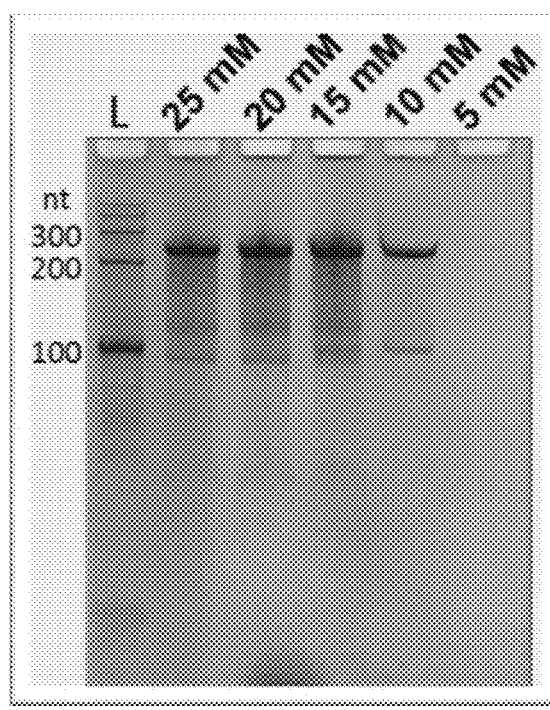
FIGS. 6A and 6B (A) The 2CZ transcription samples were checked by PAGE. The 10% polyacrylamide gel contained 8 M urea. The Mg2+ concentration in the transcription reaction varied from 5 mM to 25 mM. The reaction mixture was left at 22° C. overnight. (B) After overnight transcription, the gel formed in the reaction containing 25 mM $MgCl_2$ and no visible gel noticed in the other transcription tubes. These samples were kept in a 4° C. refrigerator. After ~2 weeks storage, the tubes containing 10, 15, and 20 mM $MgCl_2$ also formed gel at their bottom. The tube containing 5 mM $MgCl_2$ never had gel forming no matter how long stored in the 4° C. refrigerator.
Figure 6B:
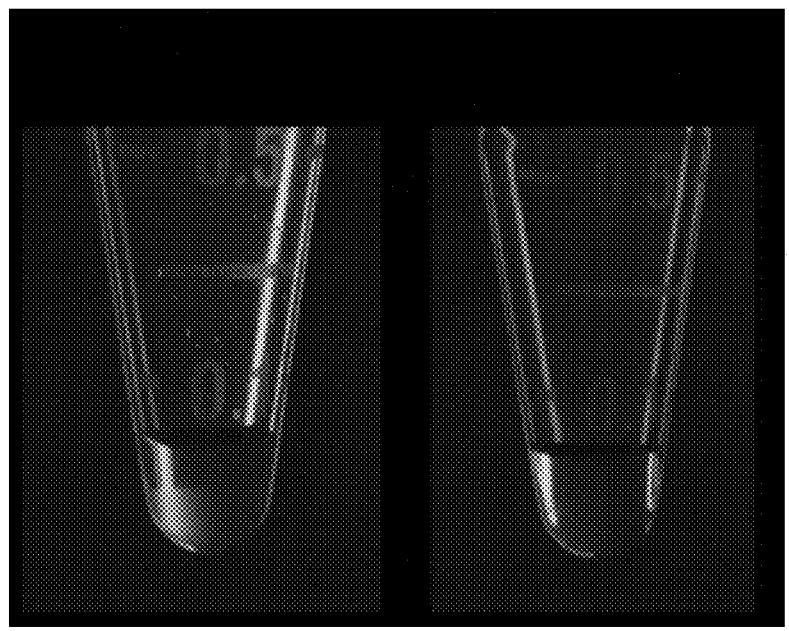

We also identified two critical residues or GC adjacent to each other in the middle of motif 1 for gelation (FIG. 4A). A single G or C is known to form canonical Watson-Crick base pair with a C or a G, respectively, through their nucleobases by hydrogen bonding (FIG. 4B)[26]. We therefore hypothesized that the GC from one CZ RNA can base-pair with CG in the same motif from another CZ RNA molecule, thereby forming a stable intermolecular loop-loop interaction. In fact, Li et al[26] have shown that a minimum of two G:C base pairs are sufficient to mechanically stabilize RNA dimers in retroviruses through this "kissing interaction" (left panel in FIG. 4B). Not surprisingly, mutating a single residue in the GC sequence in one CZ RNA created a mismatch of the GC base paring, thus destroying the intermolecular loop-loop interaction and the gel-forming ability of the mutant (provided motif 1 is removed as well: see CZ.d3 to CZ.d5 or CZ.d6 in FIG. 4A). In fact, mutation of the GC kissing interaction is strong enough to compromises packaging, viability, and infectivity of some retroviruses[27]. Furthermore, because U:A can also form canonical Watson-Crick base pairs, albeit weaker (a GC pair has three hydrogen bonds while an AU pair has two), it is conceivable that the two residues or A and U that flank the CG residues in motif 1 can base-pair U and A so that the intermolecular loop-loop interaction between the two motif 1s is further strengthened (FIG. 4B). On the other hand, the examination of the sequence in motif 2 has also allowed us to speculate that at least eight consecutive residues at the end of motif 2 (FIG. 4B, right panel) can form base pairs between the two identical loops of two CZ RNA aptamers. However, that the entire motif 2 must be removed in order to render the mutant RNA totally incapable of forming gel suggested that besides this stretch of eight residues, the stem or the step-loop in motif 2 were also involved in gel-forming property of the RNA.

The mutation experiment and analysis have shown that both motifs 1 and 2 in a CZ RNA molecule are required to form RNA network structures as the basis of the hydrogel. There are at least two interesting conclusions to be drawn from this finding. Firstly, each motif should serve as an "arm" in its own direction to extend its non-covalent contact with the same motif but from another RNA molecule. Together, the CZ RNA aptamer with the two motifs is like an "elbow joint" as the basic constructional unit to build a complex RNA network matrix, minimally thought x-y direction. In this sense, the RNA sequence of a motif should not be special. To prove this point, we engineered two special CZ RNA mutants in that one contains two motifs 1, whereas the other contains two motifs 2. The mutant with two motifs 1, which uses ACGU as canonical Watson-Crick base pairing residues, as expected, did form a gel, while the mutant with two motifs 2 didn't. Again, this result is consistent with our conclusion that motif 1/motif 1 interaction is stronger than motif 2/motif2 interaction in forming an RNA network matrix for hydrogel. Therefore, our study in essence has enabled us to identify an architectural principle by which an extensive RNA network can self-assemble through intermolecular interactions using these motifs. Second, other types of interactions may be also involved in the network folding and interactions of these RNAs, in addition to strong canonical Watson-Crick base pairing through the two corresponding two motifs (FIG. 4B). For example, that the entire motif 2 is indispensable of gel forming property of CZ RNA molecule suggests that motif 2 is involved as an entire entity in inter-molecular interaction. It is known that when two helices, especially at helical termini, are next to each other, they could become coaxially stacked, and such a substructure is thermodynamically favorable and stable[28,29]. Coaxial helical stacking is among the most important types of interaction in RNA tertiary structures[30]. In fact, we found a special motif 1 mutant, i.e., an all A loop or D17 mutant (SEQ ID NO: 15), is capable for gel formation. Furthermore, replacing both motifs 1 and 2 with an all A-loop also results a mutant (D17i2, SEQ ID NO: 16) that is capable for gel formation. It is plausible that adenine (or A) bases form a unique tertiary structure, which allows As to be packed by base stacking, similar to a three A sequence known as A-minor motif. This is because adenine lacks the exocyclic atoms of other bases. We also found that D17 (the all A-loop mutant: CGU tri-nucleotides were replaced with three As) lost biological activity of potentiating AMPA receptors. Therefore, the CGU tri-nucleotides in the wild-type sequence in the CZ aptamer are essential for the biological activity but not essential for gelation. Many existing types of RNA tertiary interactions may be prevalent as well in the extensive RNA intermolecular interactions, possibly forming sacrificial bonds (please see the article by Smith, B. L., T. E. Schaffer, M. Viani, J. B. Thompson, N. A. Frederick, J. Kindt, A. Belcher, G. D. Stucky, D. E. Morse, and P. K. Hansma. 1999. Molecular mechanistic origin of the toughness of natural adhesives, fibres and composites. Nature. 399:761-763). Such a versatile array of physical interactions can be the basis of forming a stable RNA network matrix structure that is also heterogeneous in both sizes and shapes.

The present disclosure also encompasses RNA oligonucleotides in which one or more nucleotide substitutions has been made to the nucleotide sequence of SEQ ID NO: 1 or SEQ ID NO: 2 as long as the motif structure required for hydrogel formation as described above is maintained. Examples of additional RNA oligonucleotides examined for formation of hydrogels:

```
V1.2
                                              (SEQ ID NO: 17)
5'-GCATGCTAATACGACTCACTATAGGGAGGCGGATTCGAGAATTCAAC

TGCCATCTAGGCGGCGCAAAAAACGTAAAATGGGTCATGGGAAAGGGCAG

GTGAGAGGACTAGTACTACAAGCTTCTGGACTCGGATCCGCCTCCCGGAG

AATTCAACTGCCATCTAGGCGGCGCAAAAAACGTAAAATGGGTCATGGGA

AAGGGCAGGTGAGAGGACTAGTACTACAAGCTTCTGGACTCCAATATT-3' d1.CTZ1214
                                              (SEQ ID NO: 5)
5'-GGAGAAUUCAACUGCCAUCUAGGCGGCCGAAAGGUCAUGGGAAAGGG
CAGGUGAGAGGACUAGUACUACAAGCUUCUGGACUCGGU-3' d2.CTZ1214
                                              (SEQ ID NO: 6)
5'-GGGAGAAUUCAACUGCCAUCUAGGCGGCGCAAAAAACGUAAAAUGGG
UCAUGGGAAAGGGCAGGUGAGAGGACUGAAAAGCUUCUGGACUCCC-3' d3.CTZ1214
                                              (SEQ ID NO: 7)
5'-GGGAGAAUUCAACUGCCAUCUAGGCGGCGCAAAAAACGUAAAAUGGG
UCAUGGGAAAGGGCAGGUGGGACUCCC-3' d5.CTZ1214
                                              (SEQ ID NO: 8)
5'-GGGAGAAUUCAACUGCCAUCUAGGCGGCGCAAAAAACUUAAAAUGGG
UCAUGGGAAAGGGCAGGUGGGACUCCC-3' d6.CTZ1214
                                              (SEQ ID NO: 9)
5'-GGGAGAAUUCAACUGCCAUCUAGGCGGCGCAAAAAACCUAAAAUGGG
UCAUGGGAAAGGGCAGGUGGGACUCCC-3' d7.CTZ1214
                                              (SEQ ID NO: 10)
5'-GGGAGAAUUCAACUGCCAUCUAGGCGGCGCAAAAAACUUAAAAUGGG
UCAUGGGAAAGGGCAGGUGAGAGGACUGAAAAGCUUCUGGACUCCC-3' d8.CTZ1214
                                              (SEQ ID NO: 11)
5'-GGGAGAAUUCAACUGCCAUCUAGGCGGCGCAAAAAACCUAAAAUGGG
UCAUGGGAAAGGGCAGGUGAGAGGACUGAAAAGCUUCUGGACUCCC-3' d9.CTZ1214
                                              (SEQ ID NO: 12)
5'-GGGAGAAUUCAACUGCCAUCUAGGCGGCGCAAAAAACUUAAAUGGG
UCAUGGGAAAGGGCAGGUGAGAGGACUAGUACUACAAGCUUCUGGACUCC
C-3' d10.CTZ1214
                                              (SEQ ID NO: 13)
5'-GGGAGAAUUCAACUGCCAUCUAGGCGGCGCAAAAAACCUAAAAUGGG
UCAUGGGAAAGGGCAGGUGAGAGGACUAGUACUACAAGCUUCUGGACUCC
C-3' d11.CTZ1214
                                              (SEQ ID NO: 14)
5'-GGGAGAAUUCAACUGCCAUCUAGGCGGCGCAAAAAACGUAAAAUGGGU
CAUGGGAAAGGGCAGACGGCGCAAAAAACGUAAAAUGGGUCAUGCUCC
C-3'

D17 (A-loop in motif 1):
                                              (SEQ ID NO: 15)
5'-GGGAGAAUUCAACUGCCAUCUAGGCGGCGCAAAAAAAAAAAAAUGGGU
CAUGGGAAAGGGCAGGUGAGAGGACUAGUACUACAAGCUUCUGGACUCG
GU-3'

D17i2 (two A-loops)
                                              (SEQ ID NO: 16)
5'-GGGAGAAUUCAACUGCCAUCUAGGCGGCGCAAAAAAAA
AAAAAUGGGUCAUGGGAAAGGGCAGACGGCGCAAAAAAAAAAAAAUGG
GUCAUGCUCCC-3'
```

Of these, only d5.CTZ1214 and d6.CTZ1214 have not yet been shown to form a gel.

These examples illustrate that an RNA molecule with specific sequence motifs that can interact with other RNA molecules in sufficient concentration can form a hydrogel by self-assembling into a polymeric network structure. Similar to other types of biocompatible hydrogels, RNA hydrogels may therefore be explored for similar applications such as drug delivery (in our case, the RNA itself is a potentiating aptamer for AMPA receptors). It should be noted that for these biological application, RNA hydrogels with improved mechanical and functional properties, such as a prolonged drug release controlled by RNA hydrogel degradation, could be obtained through chemical cross-linking to change mesh size, as an example. The mesh size can be readily achieved by the use of cross-linker density. The fact that 2CZ RNA aptamer, which now contains an extra stem-loop in between the two "monomeric" CZ sequence, is fully capable of forming hydrogel further suggests that additional sequences or motifs, irrelevant to hydrogel formation, can be designed as a functional platform to link other RNAs or "code" for a new function with the hydrogel. For example, this stem-loop can be replaced with an aptamer for molecular recognition and sensing.

Synthetic RNA oligonucleotides of the disclosure may be prepared by any method known to those of skill in the art, including chemical synthesis, isolation from a nucleic acid library or by recombinant technology. In one embodiment, the method of preparing a nucleic acid ligand of the invention begins by identifying nucleic acid ligands from a candidate mixture of nucleic acids by Systemic Evolution of Ligands by Exponential Enrichment (SELEX), or a variation thereof, which is a commonly used method of identifying nucleic acid ligands that bind to a target from a candidate mixture of nucleic acids.

Examples

Cell Culture and Transient Receptor Expression

The original cDNAs encoding rat GluA2Qflip AMPA receptor was kindly provided by Steve Heinemann. The GluA2Qflip receptors were transiently expressed in human embryonic kidney (HEK-2935) cell. HEK-2935 cells were maintained in Dulbecco's modified Eagle's medium supplemented with 10% fetal bovine serum and 1% penicillin in a 37° C., 5% CO2, humidified incubator. The DNA plasmids encoding green fluorescent protein and large T-antigen were cotransfected in HEK-293S cells (18). Transfected cells were used for recording 48 hour after transfection. For the in vitro selection, the transfected cells were harvested 48 hours after transfection, and the membrane fragment that contained the GluA2Qflip receptor was prepared as described (19).

In Vitro Selection

The preparation of the RNA library and the protocol of running the in vitro evolution selection were described previously (19). For binding in the initial round of selection, the RNA library with ~10$^{15}$ random sequences was dissolved in the extracellular buffer, which contained (in mM) 150 NaCl, 3 KCl, 1 CaCl$_2$, 1 MgCl$_2$, 10 HEPES (pH 7.4). The final concentration of membrane-bound receptor in the binding mix was 8 nM, as determined by [$^3$H]AMPA binding. The membrane-bound receptor was exposed to 0.4 mM of cyclothiozide (CTZ) for 5 min and then to 50 mM of glutamate for 5 min. The mixture was then mixed with the RNA library. The mixture of the RNA library and the receptor was incubated at a thermo-cycle as follow: 22° C./40 min→37° C./10 min→22° C./20 min→(37° C./5 min→22° C./20 min)×2. After the thermal cycle, the mixture were filtered through a 0.45 µm nitrocellulose filter (Millipore, HAWP02500). The filter was washed with 15 ml of 1× extracellular buffer 3 times. The filter was transferred to a fresh tube containing 0.5 ml of 10 mM Tris-HCl with 8 M urea. The tube was incubated at 95° C. for 5 min and extracted with phenol/chloroform/isoamyl alcohol (24:24:1). The RNA in the water phase was precipitated by ethanol, air-dried, and dissolved in H2O. The reverse transcription and PCR were described as previously (19). Starting from cycle 5, the RNA library was mixed with 10 mg of cell fragments, which prepared from the HEK293S cells transient transfected with TAg plasmid, and incubated at 22° C. for 20 min. The mixture was passed through a nitrocellulose filter. The solution filtered through was collected and used as the RNA library for the binding reaction. The cell membrane fragments without GluA2 was used to remove non-target binding RNA from the library. At the end of the 12th selection round, the DNA pools from rounds 10, and 12 were separately cloned into the pGEM-T easy vector (Invitrogen) for sequencing.

In one embodiment, preparation of RNA hydrogel according to the disclosure is by RNA in vitro transcription in accordance with methods known in the art using DNA templates for in vitro transcription by PCR amplification. Following transcription, the presence of a hydrogel is generally confirmed by visual inspection of the transcription reaction mixture.

DNA nucleotide sequences for in vitro transcription are as shown below.

pCTZ1214 for:

(SEQ ID NO: 3)

5'-
TAATACGACTCACTATAGGGAGAATTCAACTGCCATCTAGGCGGCGCAAA
AAACGTAAATGGGTCATGGGAAAGGGCAGGTGAGAGGACTAGTACTACA
AGCTTCTGGACTCGGT-3'.

pV1.2:

(SEQ ID NO: 4)

5'-
TAATACGACTCACTATAGGGAGGCGGATTCGAGAATTCAACTGCCATCTA

GGCGGCGCAAAAAACGTAAATGGGTCATGGGAAAGGGCAGGTGAGAGGA

CTAGTACTACAAGCTTCTGGACTCGGATCCGCCTCCCGGAGAATTCAACT

GCCATCTAGGCGGCGCAAAAAACGTAAATGGGTCATGGGAAAGGGCAGG

TGAGAGGACTAGTACTACAAGCTTCTGGACTCCA-3' pV2.2:

(SEQ ID NO: 18)

5'-
TAATACGACTCACTATAGGGAGGCGGATTCGAGAATTCAACTGCCATCTA

GGCGGCGCAAAAAACGTAAATGGGTCATGGGAAAGGGCAGGTGAGAGGA

CTAGTACTACAAGCTTCTGGACTCGGATCCGTGACCCAAAGGTCATACTC

CCGGAGAATTCAACTGCCATCTAGGCGGCGCAAAAAACGTAAAATGGGTC

ATGGGAAAGGGCAGGTGAGAGGACTAGTACTACAAGCTTCTGGACTCC

A-3'

RNA In Vitro Transcription

The RNA in vitro transcription reaction contained 0.3 µM DNA template, 10 mM of each NTPs, 50 ng/µl of T7 RNA polymerase, 0.005 unit/µl of pyrophosphatase, 25 mM of MgCl2, 10 mM DTT, 2 mM spermidine, and 50 mM HEPES (pH 7.5). The transcription mixture was incubated at 37° C. overnight and then kept in a 4° C. refrigerator.

RNA PAGE Purification

A tubular PAGE column system (Bio-Rad Prepcell 491) was used to purify RNA from the transcription mixture. The detailed method has been described previously (cite HPLC paper). The polyacrilamide gel column was formed by 80 ml of 12% acrylamide/bis-acrylamide (37.5:1) solution in 1×Tris-Borate-EDTA (TBE) buffer containing 8 M urea. For each run, about 1 ml of the transcription mixture was mixed with 1 ml of gel loading buffer II (Biorad), which contained 95% of formamide. The RNA transcription sample with loading buffer was incubated at 95° C. for 5 min and loaded on the surface of the PAGE column. The electrophoresis was run at 250 V for 10 hours. A peristaltic pump was used to regulate the mobile phase or 1×TBE buffer at 1 ml/minute flow rate. The elution of the RNA sample was monitored by a UV detector and collected in a fraction collector (BioFrac, Bio-Rad) at 1.5 ml/fraction. The fractions were then pooled based on the chromatography trace and concentrated in an Amicon filtration centrifuge tube (Millipore). The TBE buffer in the eluted samples was exchanged with 25 mM HEPES buffer by spinning in an Amicon filtration tube; the same procedure was repeated two more times. The concentration of the collected sample was determined by a Nanodrop 1000 spectrophotometer (Thermal Fisher Scientific).

REFERENCES

1 Amsden, B. Solute diffusion within hydrogels. Mechanisms and models. *Macromolecules* 31, 8382-8395, doi: DOI 10.1021/ma980765f (1998).
2 Guvendiren, M., Lu, H. D. & Burdick, J. A. Shear-thinning hydrogels for biomedical applications. *Soft Matter* 8, 260-272, doi:10.1039/c15m06513k (2012).
3 Lee, K. Y. & Mooney, D. J. Hydrogels for tissue engineering. *Chem Rev* 101, 1869-1879 (2001).
4 Slaughter, B. V., Khurshid, S. S., Fisher, O. Z., Khademhosseini, A. & Peppas, N. A. Hydrogels in regenerative medicine. *Adv Mater* 21, 3307-3329, doi:10.1002/adma.200802106 (2009).
5 Nicodemus, G. D. & Bryant, S. J. Cell encapsulation in biodegradable hydrogels for tissue engineering applications. *Tissue Eng Part B Rev* 14, 149-165, doi:10.1089/ten.teb.2007.0332 (2008).
6 Hoffman, A. S. Hydrogels for biomedical applications. *Adv Drug Deliv Rev* 54, 3-12 (2002).

7 Nicodemus, G. D. & Bryant, S. J. Cell encapsulation in biodegradable hydrogels for tissue engineering applications. *Tissue Eng Part B Rev* 14, 149-165, doi:10.1089/ten.teb.2007.0332 (2008).

8 Fichman, G. & Gazit, E. Self-assembly of short peptides to form hydrogels: design of building blocks, physical properties and technological applications. *Acta Biomater* 10, 1671-1682, doi:10.1016/j.actbio.2013.08.013 (2014).

9 Yang, H. H., Liu, H. P., Kang, H. Z. & Tan, W. H. Engineering target-responsive hydrogels based on aptamer—Target interactions. *J Am Chem Soc* 130, 6320-+, doi:10.1021/ja801339w (2008).

10 Um, S. H. et al. Enzyme-catalysed assembly of DNA hydrogel. *Nat Mater* 5, 797-801, doi:10.1038/nmat1741 (2006).

11 Noll, T. et al. Construction of Three-Dimensional DNA Hydrogels from Linear Building Blocks. *Angew Chem Int Edit* 53, 8328-8332, doi:10.1002/anie.201402497 (2014).

12 Leontis, N. B., Stombaugh, J. & Westhof, E. The non-Watson-Crick base pairs and their associated isostericity matrices. *Nucleic Acids Res* 30, 3497-3531 (2002).

13 Butcher, S. E. & Pyle, A. M. The molecular interactions that stabilize RNA tertiary structure: RNA motifs, patterns, and networks. *Acc Chem Res* 44, 1302-1311, doi:10.1021/ar200098t (2011).

14 Zhou, J., Bobbin, M. L., Burnett, J. C. & Rossi, J. J. Current progress of RNA aptamer-based therapeutics. *Front Genet* 3, 234, doi:10.3389/fgene.2012.00234 (2012).

15 Winkler, W., Nahvi, A. & Breaker, R. R. Thiamine derivatives bind messenger RNAs directly to regulate bacterial gene expression. *Nature* 419, 952-956, doi:10.1038/nature01145 (2002).

16 Ellington, A. D. & Szostak, J. W. In vitro selection of RNA molecules that bind specific ligands. *Nature* 346, 818-822 (1990).

17 Tuerk, C. & Gold, L. Systematic evolution of ligands by exponential enrichment: RNA ligands to bacteriophage T4 DNA polymerase. *Science* 249, 505-510 (1990).

18 Lynch, G. & Baudry, M. The biochemistry of memory: a new and specific hypothesis. *Science* 224, 1057-1063 (1984).

19 Lynch, G. Glutamate-based therapeutic approaches: ampakines. *Curr Opin Pharmacol* 6, 82-88 (2006).

20 Martin, S. J., Grimwood, P. D. & Morris, R. G. Synaptic plasticity and memory: an evaluation of the hypothesis. *Annu Rev Neurosci* 23, 649-711, doi:10.1146/annurev.neuro.23.1.649 (2000).

21 Carlsson, M. & Carlsson, A. Interactions between glutamatergic and monoaminergic systems within the basal ganglia—implications for schizophrenia and Parkinson's disease. *Trends Neurosci* 13, 272-276 (1990).

22 Bloss, E. B. et al. Behavioral and biological effects of chronic S18986, a positive AMPA receptor modulator, during aging. *Exp Neurol* 210, 109-117, doi:10.1016/j.expneurol. 2007.10.007 (2008).

23 Dingledine, R., Borges, K., Bowie, D. & Traynelis, S. F. The glutamate receptor ion channels. *Pharmacol Rev* 51, 7-61 (1999).

24 Huang, Z., Pei, W., Jayaseelan, S., Shi, H. & Niu, L. RNA aptamers selected against the GluR2 glutamate receptor channel. *Biochemistry* 46, 12648-12655 (2007).

25 Costa, M. & Michel, F. Rules for RNA recognition of GNRA tetraloops deduced by in vitro selection: comparison with in vivo evolution. *Embo J* 16, 3289-3302, doi:10.1093/emboj/16.11.3289 (1997).

26 Li, P. T., Bustamante, C. & Tinoco, I., Jr. Unusual mechanical stability of a minimal RNA kissing complex. *Proc Natl Acad Sci USA* 103, 15847-15852, doi:10.1073/pnas.0607202103 (2006).

27 Paillart, J. C., Shehu-Xhilaga, M., Marquet, R. & Mak, J. Dimerization of retroviral RNA genomes: an inseparable pair. *Nat Rev Microbiol* 2, 461-472, doi:10.1038/nrmicro903 (2004).

28 Walter, A. E. et al. Coaxial stacking of helixes enhances binding of oligoribonucleotides and improves predictions of RNA folding. *Proc Natl Acad Sci USA* 91, 9218-9222 (1994).

29 Walter, A. E. & Turner, D. H. Sequence dependence of stability for coaxial stacking of RNA helixes with Watson-Crick base paired interfaces. *Biochemistry* 33, 12715-12719 (1994).

30 Doherty, E. A., Batey, R. T., Masquida, B. & Doudna, J. A. A universal mode of helix packing in RNA. *Nat Struct Biol* 8, 339-343, doi:10.1038/86221 (2001).

31 Wichterle O. Hydrophilic gels for biological use. Nature 1960; 185:117.

32 Singh Anisha, Sharma Pramod Kumar, Garg Vipin Kumar, Garg Garima. Hydrogels: a review. 2010; 4(2): Article 016. ISSN: 0976-044X [September-October].

33 Amulya K. Saxena synthetic biodegradable hydrogel (Pleura Seal) sealant for sealing of lung tissue after thoracoscopic resection. J Thoracic Cardiovasc Surg 2010,139(2):496-7.

34 Hamidi Mehrdad, Azadi Amir, Rafiei Pedram. Hydrogel nanoparticles in drug delivery. Adv Drug Deliv Rev 2009,60(15):1638-49.

35 Sun X, Zhang G, Shi Q, Tang B, Wu Z J. Preparation and characterization of water-swellable natural rubbers. J Appl Polym Sci 2002; 86:3212-717.

36 Chen X, Martin B D, Neubauer T K, Linhardt R J, Dordick J S, Rethwisch D G. Enzymatic and chemoenzymatic approaches to synthesis of sugar based polymer and hydrogels. Carbohydr Polym 1995; 28:15-21.

37 Kashyap N, Kumar N, Kumar M. Hydrogels for pharmaceutical and biomedical applications. Crit Rev Ther Drug Carr Syst 2005; 22:107-49.

38 Kaihara Sachiko, Matsumura Shuichi, Fisher JohnP. Synthesis and characterization of cyclic acetal based degradable hydrogels. Eur J Pharm Biopharm 2008; 68(1):67-73.

39 Stamatialis Dimitrios F, Papenburg Bernke J, Girona's Miriam, Saiful Saiful, Bettahalli Srivatsa N M, Schmitmeier Stephanie, Wessling Matthias. Medical applications of membranes: drug delivery, artificial organs and tissue engineering. J Membr Sci 2008; 308(1-2):1-34.

40 Zhang Ling, Li Kuifeng, Xiao Wenqian, Zheng Li, Xiao Yumei, Fan Hongsong, et al. Preparation of collagen-chondroitin sulfate-hyaluronic acid hybrid hydrogel scaffolds and cell compatibility in vitro. Carbohydr Polym 2011,84(1):118-25.

41 Saul Justin M, Williams David F. Hydrogels in regenerative medicine, principles of regenerative medicine. 2nd ed.; 2011. p. 637-61.

42 Van der Linden H J, Herber S, Olthuis W, Bergveld P. Patterned dual pH responsive core shell hydrogels with controllable swelling kinetics and volume. Analyst 2003; 128:325-31.

43 Sikareepaisan Panprung, Ruktanonchai Uracha, Supaphol Pitt. Preparation and characterization of asiaticoside-loaded alginate films and their potential for use as effectual wound dressings. Carbohydr Polym 2011,83(4): 1457-69.
44 Wang Feng, Li Zhenqing, Khan Mahmood, Tamama Kenichi, Kuppusamy Periannan, et al. Injectable, rapid gelling and highly flexible hydrogel composites as growth factor and cell carriers. Acta Biomater 2010; 6(6):1978-91.
45 Roy Debashish, Cambre Jennifer N, Brent S. Sumerlin future perspectives and recent advances in stimuli-responsive materials. Prog Polym Sci 2010; 35(12):278-301.
46 Krsko Peter, McCann Thomas E, Thach Thu-Trang, Laabs Tracy L, Geller Herbert M, Libera Matthew R. Length-scale mediated adhesion and directed growth of neural cells by surface-patterned poly(ethylene glycol) hydrogels Original Research Article. Biomaterials 2009; 30(5):721-9.

We claim:

1. A synthetic RNA oligonucleotide consisting of the nucleotide sequence of SEQ ID NO: 1, 8, 9, 15 or 16.

2. A synthetic RNA oligonucleotide comprising the nucleotide sequence of SEQ ID NO: 1, 8, 9, 15 or 16.

3. A synthetic RNA oligonucleotide comprising tandem repeats of the nucleotide sequence of SEQ ID NO: 1, 8, 9, 15 or 16.

4. The synthetic oligonucleotide of claim 3 consisting of the nucleotide sequence of SEQ ID NO: 2.

5. The synthetic oligonucleotide of claim 3 comprising the nucleotide sequence of SEQ ID NO: 2.

6. The synthetic oligonucleotide of claim 3, where said tandem repeats are separated by a linking/intervening nucleotide sequence.

7. A hydrogel comprising the synthetic oligonucleotide of claim 1.

8. A synthetic oligonucleotide that encodes an RNA of claim 1.

9. A synthetic oligonucleotide of claim 8, wherein the oligonucleotide consists of the nucleotide sequence of SEQ ID NO: 3.

10. The synthetic oligonucleotide of claim 8, wherein the oligonucleotide consists of the nucleotide sequence of SEQ ID NO: 4.

11. A pharmaceutical composition comprising a synthetic oligonucleotide consisting of the nucleotide sequence of SEQ ID NO: 1, 2, 8, 9, 15 or 16.

12. A pharmaceutical composition comprising a hydrogel comprising an oligonucleotide with the nucleotide sequence of SEQ ID NO: 1, 2, 8, 9, 15 or 16.

* * * * *